United States Patent [19]

Enhorning

[11] Patent Number: 4,800,750
[45] Date of Patent: Jan. 31, 1989

[54] DEVICE FOR ACCURATELY DISPLACING FLUID

[76] Inventor: Goran Enhorning, 21 Oakland Pl., Buffalo, N.Y. 14222

[21] Appl. No.: 61,122

[22] Filed: Jun. 10, 1987

[51] Int. Cl.⁴ .............................................. G01N 13/02
[52] U.S. Cl. ......................................................... 73/64.4
[58] Field of Search ........................................... 73/64.4

[56] References Cited

U.S. PATENT DOCUMENTS 3,854,324 12/1974 Altshuler et al. ................. 73/64.4 X
3,881,344  5/1975 Jobe ...................................... 73/64.4

FOREIGN PATENT DOCUMENTS 238272  8/1986 German Democratic
              Rep. ....................................... 73/64.4

Primary Examiner—John Chapman
Assistant Examiner—Joseph W. Roskos
Attorney, Agent, or Firm—Christel, Bean & Linihan

[57] ABSTRACT

A device for accurately displacing a fluid within a chamber. The device includes a barrier wall (38) which separates the fluid (12) to be displaced from another fluid, a rod (32) and a concentric elastomeric tube (34) disposed about the rod and passing through an aperture in the barrier wall, securing structure (58) which secures the ends of the elastomeric tube (34) about the rod (32), a resilient annular element (44) carried by a cavity (48) formed within the barrier wall, and structure to compress the resilient element so that it is forced radially inwardly to seal the resilient tube about the rod. The space between the rod (32) and the tube (34) to either side of the resilient element (44) is filled with a lubricant.

11 Claims, 1 Drawing Sheet

DEVICE FOR ACCURATELY DISPLACING FLUID

TECHNICAL FIELD

The present invention relates generally to a device for accurately displacing fluid, and more particularly to such a device wherein linear displacement of an element will displace fluid.

BACKGROUND OF THE INVENTION

There is frequently a need to very accurately displace a fluid. For example, in apparatus used in the pulsating bubble technique for evaluating the surface tension of a pulmonary surfactant requires that precise fluid quantities be displaced in order to properly evaluate the surface tension of the fluid being displaced. Such an apparatus is shown in Prog. Resp. Res., vol. 15, pp. 57–61 and also J. Appl. Physiol.: Respirat. Eviron. Exercise Physiol. 43 (2): pp 198–203, 1977. It has been found that in the prior apparatus that linear movement of a fluid displacing device could not be translated directly into the quantity of fluid being displaced, primarily due to seal movement. In addition, it has been found that fluid to one side of the seal could contaminate fluid to the other side of the seal.

OBJECTS AND SUMMARY OF THE INVENTION

It is an object of the present invention to therefore provide a device which can more accurately displace fluids than prior art known devices.

More specifically, it is an object of the present invention to provide a device for accurately displacing fluid wherein linear movement of an elongated element can be correlated directly to the fluid volume to be displaced.

It is a further object of the present invention to provide a device for displacing fluid wherein fluid to one side of a barrier wall cannot contaminate fluid to the other side of the barrier wall.

The above is accomplished by providing a barrier wall which separates the fluid to be displaced from another fluid. An elongated element having a constant cross section is extended through the barrier wall and also an elastomeric tube which surrounds the elongated element. The ends of the elastomeric tube are secured to the elongated element, and sealing means are provided which are carried by the wall and which seal an intermediate portion of the elastomeric tube about the elongated element. The space between the tube and the elongated element is filled with a lubricant. Displacement of the elongated element into or out of the fluid will cause a displacement of fluid equal in volume to the volume of the element, which volume is directly proportional to the length of the elongated element. As the only movement through the barrier wall is of the rod which is surrounded by a lubricant in a tube sealed to the rod, it is virtually impossible for fluid to one side of the barrier wall to contaminate fluid to the other side in normal use.

The above objects and other objects and advantages of this invention will become more apparent after a consideration of the following detailed description taken in conjunction with the accompanying drawings in which a preferred form of this invention is illustrated.

DETAILED DESCRIPTION

Figure 1:
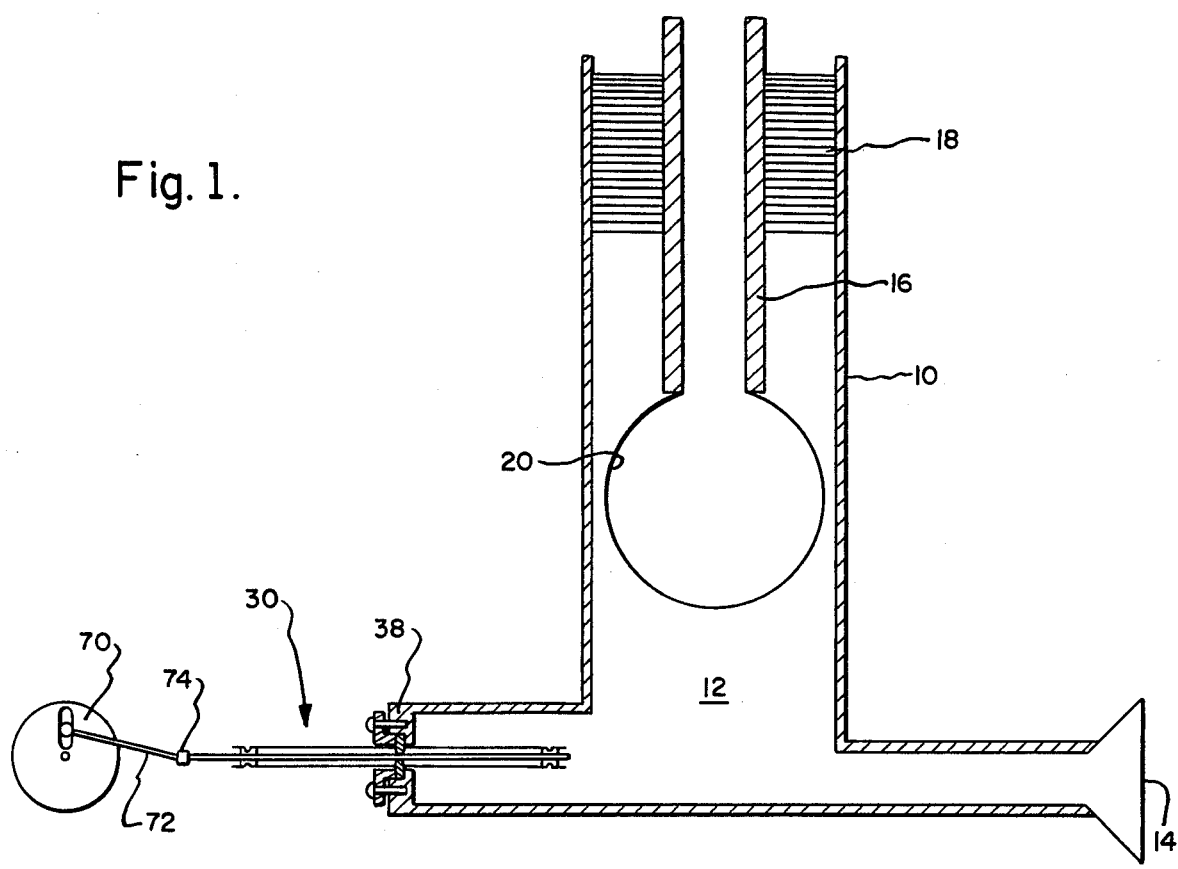
FIG. 1 is a view illustrating an apparatus in which the device of this invention may be utilized for displacing precise quantities of fluid, some portions of the apparatus being shown in greater scale than other portions.

As the device of the present invention has use in an apparatus associated with the pulsating bubble technique for evaluating the surface tension of a pulmonary surfactant, such an apparatus is illustrated in FIG. 1 in association with the device of this invention. Such an apparatus includes a chamber 10 filled with the fluid 12 which is to be displaced. A portion of the chamber is connected to a pressure transducer 14. A capillary 16 extends into the chamber, the capillary being sealed to the chamber by suitable sealing means 18. By accurately displacing the fluid within the chamber 10 a bubble 20 may be formed below the capillary 16. If the bubble is caused to be pulsated within precisely defined limits, by measuring the pressure at 14 the surface tension of the fluid surrounding the bubble can be determined.

In the prior art apparatus of the type referred to immediately above the fluid has been displaced by utilizing a small diameter piston which is caused to be reciprocated back and forth within a cylinder by means of a crank rod assembly. However, as the O-rings which engage the cylinder wall will tend to shift as the piston is caused to change its direction of travel if it is not possible to directly correlate the movement of the piston to the displacement of the fluid. In addition, fluid to one side of the O-ring will tend to contaminate fluid to the other side of the O-ring as the piston reciprocates in and out of the cylinder. Of course, leakage becomes worse as the O-ring wears. Furthermore, there is a relatively high frictional force which must be overcome as the piston reciprocates in and out of the piston which friction tends to accelerate the wear of the O-ring.

By utilizing the device of the present invention, such a direct linear correlation can be achieved. In addition, it is possible to achieve an essentially leak proof seal having very little friction. The device of this invention is indicated generally at 30 and includes an elongated element 32 in the form of a stainless steel rod, and an elastomeric tube 34, the ends of which are secured to the rod 32. Both the tube 34 and rod 32 pass through an aperture 36 formed within barrier wall 38 which, as can be seen from FIG. 1, may be part of the chamber 10. The elastomeric tube is preferably made of silicone rubber, and the space between the tube 34 and the elongated element 32 is filled with a lubricant 40 which will typically be silicone oil when a silicone rubber tube 34 is utilized. The rod 32 is of constant cross section and one end 32a terminates within the fluid 12 which is to be displaced.

Figure 2:
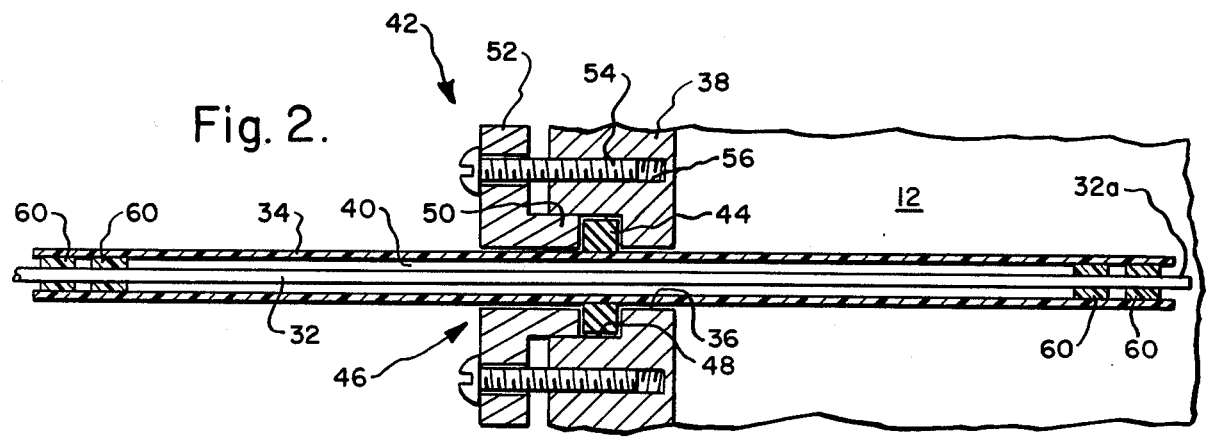
FIG. 2 is an enlarged detail of the device shown in FIG. 1, the parts being shown partially assembled.

In accordance with the principles of this invention sealing means, indicated generally at 42, are provided which are carried by the barrier wall and which seal an intermediate portion of the elastomeric tube 34 about the elongated element 32 in such a manner that a fluid tight seal is achieved about the element 32 but which permits movement of the element through the sealing means. The sealing means includes an annular resilient element 44, which may be a rubber washer, and clamping means, indicated generally at 46. The clamping means is capable of deforming the annular resilient element radially inwardly from the partially assembled position shown in FIG. 2 to the fully assembled position shown in FIG. 3. When fully assembled, the elastomeric tube 34 is held in contact with the elongated tube in such a manner that a fluid tight seal is achieved, but which permits low friction movement of the elongated element through the sealing means. The clamping means includes a cavity 48, which cavity is preferably formed in the barrier 38. The clamping means further includes a rigid annular element 5 provided with a flange 52 which is engaged by a plurality of linear displacement means in the form of screws 54. The head of the screws will bear against the outer surface of the flange 52 and the inner end of the screws 54 are received within threaded holes 56 in the barrier wall 38. It can be seen from a comparison of FIGS. 2 and 3 that by tightening down the screws the annular resilient element 44 will be forced radially inwardly until an intermediate portion of the tube 34 is properly sealed about the rod 32.

The securing means for securing the ends of the elastomeric tube to the rod 32 are indicated generally at 58 and include two pairs of washers 60, there being one pair of washers at each end of the elastomeric tube. The washers are carried by the elongated element 32 in such a manner that they will not slide on the element 32. In addition, there is a small gap 62 between each pair of washers. The securing means further includes ties, which may be sutures 64, which are disposed about the tube 34 and are sufficiently tight so as to force a portion of the tube into the gap 62 between the washers 60 thereby securing the tube to the rod.

Figure 3:
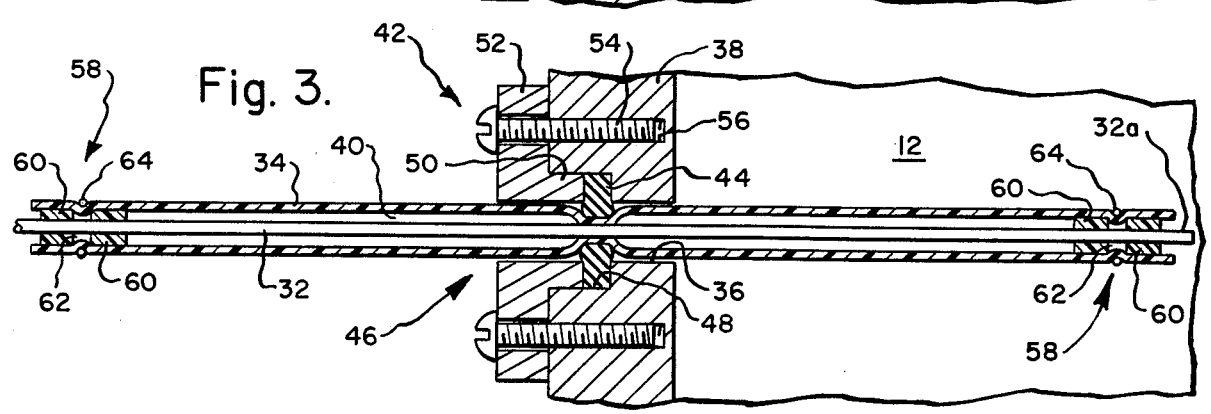
FIG. 3 is a view similar to FIG. 2 but showing the parts after they had been assembled together in their complete operative positions.

In operation, if the tube is moved to the right, the volume of the fluid which is displaced will correspond to the volume of the rod which moves into the fluid. As the rod 32 has a constant cross section, the displaced fluid will be directly proportional to the linear movement of the rod. It should also be noted that as the rod moves into the fluid nothing else would be introduced into the fluid to be displaced. Therefore, the lubricant disposed between the tube 34 and rod 32 is sealed from movement from one side of the barrier 38 to the other side when the parts are in their fully assembled position as shown in FIG. 3. In addition, the tube 34 when fully assembled cannot move from one side to the other side of the barrier wall 38 and therefore both the volume of the tube and the volume of the lubricant within the chamber 10 remains constant. Fluid to one side of barrier wall 38 cannot contaminate fluid to the other side of the barrier wall.

When the present invention is utilized with a pulsating bubble apparatus it will be driven by a rotating crank mechanism including disk 70, connecting rod 72, and a slakless universal joint 74. The connecting rod is secured to the disk 70 in such a manner that its throw may be varied, this feature being well known in the art and therefore not being illustrated in the present drawings.

While the device of the present invention has been disclosed in conjunction with a pulsating bubble apparatus, it should be appreciated that it may be used in other forms of apparatus. Thus, it may be used in a precision pipette similar to that sold under the trade name of "Eppendorf". Other applications of this device will occur to those having ordinary skill in the art. For example, if the fluid to one side of the barrier wall is a lubricant of the same type as lubricant 40, it is not necessary to seal the tube to rod 32 on that side, it only being necessary that a leak proof seal be maintained in the area of the barrier wall. In addition, if the fluid to one side of the barrier wall is corrosive to the metal of rod 40, the rod will terminate within the sealed end of tube 34.

While a preferred structure in which the principles of the present invention have been incorporated is shown and described above, it is to be understood that this invention is not to be limited to the particular details shown and described above, but that, in fact, widely differing means may be employed in the broader aspects of this invention.

What is claimed is:

1. A device for accurately displacing fluid, said device comprising:
   a barrier wall separating the fluid to be displaced from another fluid, said barrier wall being provided with an aperture;
   an elongated element extending through said aperture in the barrier wall, said elongated element having a constant cross section throughout its length;
   an elastomeric tube disposed about said elongated element, an intermediate portion extending of said tube through said aperture in said barrier wall;
   securing means securing said tube to said elongated element;
   a lubricant filling the space between said elastomeric tube and said elongated element;
   sealing means carried by said barrier wall and sealing an intermediate portion of said elastomeric tube about said elongated element in such a manner that a fluid tight seal is achieved but which permits movement of said elongated element through said sealing means.

2. The device as set forth in claim 1 wherein said elastomeric tube is formed of silicone rubber.

3. The device as set forth in claim 1 wherein said lubricant is a silicone oil.

4. The device as set forth in claim 1 wherein said elongated element is a stainless steel rod.

5. The device as set forth in claim 1 wherein said sealing means includes an annular resilient element disposed about said elastomeric tube, and clamping means which deforms said resilient element radially inwardly about said elastomeric tube.

6. The device as set forth in claim 5 wherein said clamping means includes a cavity defining structure which receives said annular resilient element, a rigid annular element, and linear displacement means which forces said rigid annular element towards said cavity whereby said annular resilient element is forced radially inwardly.

7. The device as set forth in claim 6 wherein the linear displacement means are a plurality of screws.

8. The device as set forth in claim 7 wherein said cavity defining structure is a portion of said barrier wall, and said screws are received within threaded holes formed within said barrier wall.

9. The device as set forth in claim 1 wherein the securing means secures opposite ends of said elastomeric tube to said elongated element.

10. The device as set forth in claim 9 wherein the securing means includes two pairs of washers, one pair at each end of the elastomeric tube, the washers being carried by the elongated element in such a manner that they will not slip with respect to said elongated element, and there being a small gap between the washers of each pair, and ties disposed about opposite end portions of the elastomeric tube, each tie forcing a portion of the elastomeric tube into the gap between each pair of washers to secure the elastomeric tube to the washers.

11. A device for accurately displacing fluid, said device comprising:
- a barrier wall separating the fluid to be displaced from another fluid, said barrier wall being provided with an aperture;
- an elongated element extending through said aperture in the barrier wall, said elongated element having a constant cross section throughout its length, one end of the elongated element terminating within the fluid to be displaced;
- an elastomeric tube surrounding the elongated element, an intermediate portion extending of said tube through said aperture in said barrier wall;
- securing means securing opposite ends of said tube to said elongated element, said securing means including two pairs of washers, one pair being located at each end of the elastomeric tube, the washers being carried by the elongated element in such a manner that they will not slip with respect to the elongated element, there being a small gap between the washers of each pair, and ties disposed about opposite end portions of the elastomeric tube, each tie forcing a portion of the elastomeric tube into the gap between each pair of washers to secure the elastomeric tube to the washers;
- a lubricant filling the space between said elastomeric tube and the elongated element; and
- sealing means carried by said barrier wall and sealing an intermediate portion of said elastomeric tube about said elongated element in such a manner that a fluid tight seal is achieved but which permits movement of said elongated element through said sealing means, said sealing means including an annular resilient element disposed about the elastomeric tube, a cavity defining structure carried by said barrier wall which receives said annular resilient element, a rigid annular element, and screws engaging a portion of said rigid annular element and extending into threaded holes within the cavity defining structure, said screws forcing the rigid annular element into the cavity and deforming the resilient annular element radially inwardly.

* * * * *